United States Patent [19]

Caboche

[11] Patent Number: 5,493,014
[45] Date of Patent: Feb. 20, 1996

[54] HYPOCARIOGENIC HYDROGENATED STARCH HYDROLYSATE, PROCESS FOR PREPARING IT AND THE APPLICATION OF THIS HYDROLYSATE

[75] Inventor: Jean-Jacques Caboche, Bethune, France

[73] Assignee: Roquette Freres, Lestrem, France

[21] Appl. No.: 998,604

[22] Filed: Dec. 30, 1992

[30] Foreign Application Priority Data

Mar. 19, 1992 [FR] France ................... 92 03312

[51] Int. Cl.⁶ .............. C08B 30/18; C08B 30/20; C08B 30/12
[52] U.S. Cl. .............. 536/103; 536/123.1; 536/123.13; 435/95; 435/96; 435/99; 435/100; 435/101; 127/29; 127/38
[58] Field of Search .................. 514/53, 54, 58, 514/59; 426/658, 661; 536/103, 123.1, 123.13; 435/95, 96, 99, 100, 101; 127/29, 38

[56] References Cited

U.S. PATENT DOCUMENTS

| | | | |
|---|---|---|---|
| 2,436,967 | 3/1948 | Leuck | 127/29 |
| 3,766,165 | 10/1973 | Rennhard | 127/29 |
| 4,279,931 | 5/1979 | Verwaerde et al. | 426/48 |
| 4,346,116 | 5/1980 | Freres | 426/48 |
| 4,382,962 | 5/1983 | Devos et al. | 426/3 |
| 4,497,846 | 2/1985 | Boursier et al. | 426/660 |
| 4,965,354 | 2/1988 | Yanaki et al. | 536/124 |
| 5,051,500 | 8/1989 | Elmore | 536/50 |

FOREIGN PATENT DOCUMENTS

| | | |
|---|---|---|
| 0171964 | 7/1985 | European Pat. Off. |
| 0368451 | 9/1989 | European Pat. Off. |
| 1-12761 | 10/1985 | Japan |
| 2-163101 | 12/1988 | Japan |

OTHER PUBLICATIONS

Sigma Technical Note No. TDFAB-1, Jun. 91.
"J. Assoc. Off. Anal. Chem" vol. 68, No. 2, 1985, p. 399.
"Starch Chemistry and Technology"—Second edition Edited by Roy L. Whistler, 1984, Academic Press Inc.
Chemical Abstracts, vol. 38, No. 7, 1944, Columbus, Ohio, US, Abstract No. 1658–89.

*Primary Examiner*—Marian C. Knode
*Assistant Examiner*—Francisco C. Prats
*Attorney, Agent, or Firm*—Larson and Taylor

[57] ABSTRACT

The subject of the invention is a hypocariogenic hydrogenated starch hydrolysate. This hydrolysate is characterized in that it has a concentration of 0.1 to 19% by weight of sorbitol, a concentration of 35 to 87% by weight of maltitol, a concentration of 1 to 17% by weight of polysaccharides which are not hydrolysed by amyloglucosidase in an F test, the balance for 100% consisting of hydrogenated oligo- or polysaccharides. This hydrolysate can be used as sweetening agent or as texturing agent in products intended to be ingested by humans or animals, especially in sweets and chewing gums as well as in syrups and food or pharmaceutical elixirs.

27 Claims, 1 Drawing Sheet

5,493,014

HYPOCARIOGENIC HYDROGENATED STARCH HYDROLYSATE, PROCESS FOR PREPARING IT AND THE APPLICATION OF THIS HYDROLYSATE

SUMMARY OF THE INVENTION

The subject of the invention as a hypocariogenic hydrogenated starch hydrolysate which can be used as sweetening agent or as texturing agent in products intended to be ingested by humans or animals, that is to say in particular in food products and in some pharmaceutical or veterinary products.

The invention also relates to the process for preparing the said hydrolysate as well as to the application of this hydrolysate in products intended to be ingested by humans or animals.

The expression "products intended to be ingested by humans or animals" is understood to mean products intended for ingestion and for oral administration such as various foodstuffs like confectionery products, pastries, creams, drinks, jams, sauces, ice creams, prepared animal fodder as well as pharmaceutical, veterinary, dietary or heath products such as for example elixirs and cough syrups, lozenges or tablets, chewy pastes, chewing gums, pastilles, mouthwashes and toothpastes.

The expression "hypocarogenic hydrogenated starch hydrolysate" is understood to mean a hydrogenated starch hydrolysate which is acidified to a lesser degree by the bacteria present in the mouth than conventional sugars such as sucrose, glucose or fructose.

BACKGROUND OF THE INVENTION

Such hypocariogenic hydrogenated starch hydrolysates are already known. There may thus be mentioned, for example maltitol syrups containing about 50–55% and containing about 72–78% maltitol relative to the dry matter. Such syrups are thus marketed for example under the trade marks "LYCASIN 80/55" and "75/75" respectively, by the applicant company. There may also be mentioned the maltitol syrups sold under the trade marks "MALTIDEX 100", "MALTIDEX 200", "MALBIT", and "FINMALT".

However, these hypocariogenic hydrogenated starch hydrolysates are not completely satisfactory.

The problems encountered can be of several types.

Thus, for example, some of these syrups or finished items in which they are used can be criticized for a lack of sweetening power.

Furthermore, the viscosity of these syrups is sometimes inadequate and in such a case, the finished items in the composition of which they are used lack "body" or texture. It is then necessary to add viscosity-promoting agents such as carboxymethylcellulose (CMC) or plant gums whose incorporation is difficult.

Other disadvantages, of an essentially technological nature, affect the use of some hypocariogenic hydrogenated starch hydrolysates when they are used for example in the manufacture of boiled sweets. The first of these disadvantages lies in a flow or plastic flow phenomenon (or so-called "cold flow" phenomenon) the center of which is the constituent material of the sweet. This phenomenon, which proves to be quite slow at 20° C. but which accelerates with increase in temperature, manifests itself in the long run by deformation of the sweets, which is detrimental to their marketing. The second disadvantage lies in the substantial hygroscopic character of these sweets, due to the fact that confectionery products need to have a water content of less than 2%, preferably less than about 1%, which results in a tendency to regain water during storage.

Some of these hydrogenated starch hydrolysates can also be criticized for not being sufficiently hypocariogenic. It is quite obvious that much more pronounced hypocariogenic properties are required in an application such as the manufacture of boiled sweets, which by virtue of their very nature risk being in prolonged contact with the teeth,-than in an application such as for example the manufacture of very dilute liquid product.

Very specific hydrogenated starch hydrolysates have thus been prepared and developed by the applicant company, most particularly for this application in boiled sweets, these hydrolysates having the characteristic of being directly usable for the manufacture of the said sweets while at the same time possessing completely satisfactory hypocariogenic properties, even enabling them to be described as "non-cariogenic" in countries like Switzerland where official methods for the determination of the non-cariogenicity of products have been introduced. The optimum hypocariogenic properties of these hydrolysates, marketed under the trade mark "LYCASIN 80/55", may be obtained by preserving a concentration of less than 3%, and preferably of less than 1.5% of hydrogenated polysaccharides corresponding to a DP greater than 20, in addition to a defined concentration of hydrogenated products corresponding to DP1 and DP2. These specific hydrogenated starch hydrolysates are described for example in U.S. Pat. Nos. 4,279,931 and 4,346,116.

Very satisfactory hypocariogenic properties can also be obtained, without any problem, with hydrolysates having a high maltitol concentration, as is the case for example for the hydrolysates marketed by the applicant company under the trade mark "MALTISORB 75/75". But these hydrolysates cannot be satisfactorily used in certain applications like that precisely of boiled sweets, jellies or cough syrups where another disadvantage is encountered which lies in the risks of crystallization occurring during the use of these hydrolysates.

All these disadvantages—lack of sweetening power, poor technological features, insufficient hypocariogenic properties, risks of crystallization—are not simultaneously encountered in the same hydrogenated starch hydrolysate. But the problem lies in the fact that the attenuation of certain disadvantages results in the aggravation of others.

Thus, for example, hydrogenated starch hydrolysates (which will be called in the following text HSH) can be obtained which possess a good sweetening power and satisfactory hypocariogenic properties. This is the case for HSHs containing a high maltitol concentration. But these hydrolysates now present risks of crystallization or they lack viscosity and cannot be used in certain major applications such as the manufacture of sweets.

Conversely, HSHs can be obtained which possess a good viscosity—thus conferring adequate "body" or texture on the items in which they are used—and which are capable of being used for example in the manufacture of sweets without causing problems of plastic flow or hygroscopicity, but unfortunately these hydrolysates are now acutely deficient in sweetening power and in particular do not possess the required hypocariogenic properties.

As mentioned above, the applicant company has already undertaken major research studies in order to try to resolve this technical problem and has in particular developed the hydrogenated starch hydrolysates known under the trademark "LYCASIN 80/55". But although these hydrolysates represented a decisive improvement, which in fact resulted in a major commercial success, they still continue to be only the result of a compromise between the contradictory properties which were mentioned above and therefore still partially possess the disadvantages which are the lack of sweetening power and relatively limited technological features in certain applications.

The applicant company, aware of these problems, has tried hard to reduce them by proposing, in European Patent No. 0,094,292, the incorporation into hydrogenated starch hydrolysates intended for the manufacture of boiled sweets an effective amount of gum arabic or carboxymethylcellulose as well as, optionally, an amount of mannitol which may be as high as 10% by weight.

However, while it is true that this addition to HSHs of gum arabic and/or carboxymethyl cellulose and optionally mannitol has made it possible to improve their behavior in the manufacture of boiled sweets, with respect to the regain of water and to plastic flow, it remains nevertheless the case that further progress is still required. In particular, as far as the optimization of the sweet manufacturing process is concerned, it would be useful to further reduce the boiling times and the manufacturing times so as to be able to use traditional confectionery materials and no longer the installations specifically developed for sugar-free confectionery. It is evident that this would indeed result in a reduction in the costs of production. Furthermore, during the boiling of the HSHs for the manufacture of sweets, the use of products such as gum arabic or carboxymethyl cellulose, which have a high viscosity in solution, sometimes render the application of vacuum difficult because of a clear tendency to foam. Moreover, the addition of gum arabic and/or CMC and/or mannitol makes it necessary for the user to carry out additional mixing, making this technique impractical and more costly.

Finally, such products can have detrimental effects on the confectionery items themselves, namely: the development of a brown color and a caramel taste which are undesirable. These disadvantages are encountered not only with boiled sweets but also, although to a lesser degree, with items such as gums, jellies or chewy pastes.

DETAILED DESCRIPTION OF THE INVENTION

A hydrogenated starch hydrolysate is therefore currently still being sought which exhibits a high sweetening power, therefore not necessarily requiring the addition of artificial sweeteners, which does not exhibit risks of crystallization, which exhibits excellent hypocariogenic properties, which exhibits good technological features in all types of application—and in particular in the manufacture of items requiring boiling—which makes it possible to confer on the items in which it is used sufficient "body" and texture, which does not require the addition of additives or auxiliary products, and finally which can be obtained from starch.

The applicant company has succeeded in reconciling all these objectives, reputed incompatible up until now, by preparing, at the cost of numerous research studies, a completely specific composition containing hydrogenated starch hydrolysate.

The hydrogenated starch hydrolysates conforming to the invention are thus characterized in that they have, the concentrations being expressed by weight relative to the dry matter of the hydrolysate:

a concentration of 0.1 to 19% of sorbitol a concentration of 35 to 87% of maltitol a concentration of 1 to 17%, preferably 1.5 to 15%, and still more preferably 2 to 12% by weight of polysaccharides which are not hydrolysed by amyloglucosidase in an F test described below, the balance for 100% consisting of hydrogenated oligo- or polysaccharides.

By virtue of the presence of a defined concentration of sorbitol and in particular of maltitol, the hydrogenated starch hydrolysates conforming to the invention have an acceptable sweetening power and which can even be high in the case where the maltitol concentration exceeds about 65%; and by virtue of the presence of the appropriate concentration of polysaccharides which are not hydrolysed by amyloglucosidase, they have completely satisfactory technological features, make it possible to confer on the items in which they are incorporated adequate "body" and texture, do not crystallize and have excellent hypocariogenic properties.

In order to determine on the hydrolysates the concentration of products which are not hydrolysed by the enzyme amyloglucosidase, the F test is used which in fact corresponds to the test for the determination of "total food fibers" developed by the company SIGMA Chemical Company (P.O. Box 14508, St Louis, Mo. 63178 U.S.A.) and which is described in the SIGMA technical note No TDFAB- 1 of Jun. 1991. This test consists essentially in determining the amount of material contained in the hydrolysate which is not hydrolysed by an amyloglucosidase in the presence of a thermoresistant α-amylase and a protease. This amount is expressed in percentage relative to an amount of about 1 g of hydrolysate previously dried under vacuum at 70° C., overnight.

To carry out this test, the procedure is as follows:

1) Four samples of about 1 g of hydrolysate previously dried under vacuum and cooled in a desiccator overnight are weighed to within 0.1 mg, and are introduced into a 400 ml tall-shaped beaker.

2) 50 ml of a phosphate buffer (0.05 M) at pH:6.0, are added to each of the four beakers.

3) 0.05 ml of a solution of alpha-amylase (Sigma product No. A 3306) is added to each of the beakers and mixed thoroughly.

4) Each beaker is covered with an aluminum foil before being placed in a boiling water bath in order to incubate them for 30 min starting from the moment when the temperature in the beakers reaches 95° C. The mixture is stirred gently at regular 5 minute intervals.

5) The solutions are cooled to room temperature.

6) The pH of the solutions is adjusted to 7.5±0.1 by adding to each beaker 10 ml of 0.171N NaOH. The pH is checked and adjusted where appropriate with sodium hydroxide (0.171 N) or phosphoric acid (0.205 M).

7) 5 mg of protease powder (Sigma product no. p-3910) are added to each of the beakers.

8) The beakers are covered with an aluminum foil and they are incubated at 60° C. for 30 min, with continuous stirring. The incubation time of 30 min starts from the moment when the internal temperature of the beakers reaches 60° C.

9) The mixture is cooled to room temperature.

10) 10 ml of 0.205 M of $H_3PO_4$ are added to each of the beakers in order to adjust the pH to 4.5±0.2. The pH is checked. It is carefully adjusted where appropriate with the sodium hydroxide or phosphoric acid solutions.

11) 0.3 ml of amyloglucosidase (Sigma product no. A.9913) is added to each beaker.

12) Each of the beakers is covered with an aluminum foil and incubated for 30 minutes at 60° C., with continuous stirring. The incubation time of 30 min starts from the moment when the internal temperature of the beakers reaches 60° C.

13) 280 ml of 95% ethanol (v/v), preheated to 60° C., are added to each of the beakers. (95% ethanol v/v: 50 ml of demineralized water, pure alcohol complement to 1000 ml at 20° C.).

14) A precipitate is allowed to form by allowing the mixtures to stand at room temperature for at least 60 minutes, or overnight (the same time for each of the 4 tests).

15) The contents of each of the beakers are filtered under vacuum over a sintered glass crucible and Celite bed, and they are successively and carefully washed with:

three times 20 ml of 78% ethanol (v/v) (78% ethanol v/v: 220 ml of demineralized water, pure ethanol complement to 1000 ml at 20° C.)

two times 10 ml of 95% ethanol (v/v)

and two times 10 ml of acetone.

16) The four filters are dried overnight at 70° C. under vacuum.

17) These filters are cooled in a desiccator before being weighed to within 0.1 mg, this weight being regarded as the sum of the weight of the filtration residue (polysaccharides not hydrolysed by amyloglucosidase, plus proteins plus ash) and the weight of the crucible with Celite.

18) The protein concentrations of two of the four filtration residues resulting from the four tests are determined by proceeding according the Kjeldahl method, using a correction coefficient of 6.25.

19) The amounts of ashes are determined on the other two filtration residues by placing the crucibles in an oven at 525° C. for 5 hours.

20) The amounts of polysaccharides not hydrolysed by amyloglucosidase are calculated for the four tests as indicated in the Sigma technical note and a mean is calculated for these amounts which is expressed in terms of the mean of the amounts of hydrolysate material dried overnight at 70° C. under vacuum, taking into account in the calculation the results of the four blank tests (without dry hydrolysate) carried out in parallel.

This F test constitutes a variant of the test for the determination of total food fibers in foodstuffs described in "J. Assoc. Off. Anal. Chem." Vol 68, No. 2, 1985, p.399.

It has the advantage of being standardized, of being able to be carried out by means of a complete analytical kit and of being repeatable and reproducible.

This being the case, the hydrogenated starch hydrolysates conforming to the invention can also be characterized by their concentration of polysaccharides which can be precipitated in ethanol and are not hydrolyzed by amyloglucosidase, this concentration being determined according to another test, termed A, which is carried out on the polysaccharide fraction previously precipitated in ethanol.

In order to determine on the hydrolysates the concentration of products which can be precipitated in ethanol and are not hydrolysed by the enzyme amyloglucosidase, the procedure is carried out as follows.

A sample of 10 grams of hydrogenated starch hydrolysate, adjusted to a Brix of 75±0.2, equivalent to a refractive index of about 1.478, is used for the determination of the level of polysaccharides which can be precipitated in ethanol. It is recalled that Brix is a unit of measurement which is commonly used in the starch industry and that the Brix of a syrup is very easily determined by a refractometer reading. A Brix of 75 corresponds, for the hydrogenated starch hydrolysates to which the invention relates, to a dry matter of about 75%.

The sample of 10 g of HSH at 75 Brix is supplemented with 30 $cm^3$ of distilled water and 60 $cm^3$ of absolute ethanol. The mixture is allowed to stand for 1 hour at 0° C. It is then centrifuged at 0° C. for 15 minutes at 10,000 g.

The pellet obtained is dried in a vacuum oven maintained at 80° C.

The weight of the precipitate obtained, $p_1$, represents the weight of polysaccharides which can be precipitated in ethanol contained in the 10 g of starting sample.

In order to determine the concentration in the hydrolysate of polysaccharides which can be precipitated in ethanol and are not hydrolysed by amyloglucosidase, a test A is used which consists in subjecting the ethanol precipitated polysaccharides previously obtained to an enzymatic attack using a thermoresistant $\alpha$-amylase, a protease and an amyloglucosidase, and then in precipitating the polysaccharides which are not hydrolysed with 95% ethanol, in filtering the precipitate thus obtained, in washing the latter several times with alcohol and with acetone, and finally in determining the weight, $P_2$, of the residue obtained.

This test is also described in "J. Assoc. Off. Anal. Chem." vol 68, no. 2, 1985, p. 399, to which reference may be made.

The hydrogenated starch hydrolysates conforming to the invention can thus be characterized in that they have, the concentrations being expressed by weight relative to the dry matter of the hydrolysate:

a concentration of 0.1 to 19% of sorbitol a concentration of 35 to 87% of maltitol a concentration of 1 to 20%, preferably 1 to 10%, and still more preferably 1.5 to 8% by weight of polysaccharides which can be precipitated in ethanol and are not hydrolysed by amyloglucosidase in the A test described above, the balance for 100% consisting of hydrogenated oligo- or polysaccharides.

According to a particular embodiment of the invention, the hydrogenated starch hydrolysates according to the invention according to the invention have a concentration of polysaccharides which can be precipitated in ethanol and are not hydrolysed by amyloglucosidase in the A test, of between 2 and 5% by weight.

Preferably, the hydrolysates conforming to the invention have a sorbitol concentration of between 1 and 17% by weight, and still more preferably of between 2 and 16% by weight.

They preferably have a maltitol concentration of between 40 and 82% by weight, and still more preferably of between 45% and 77% by weight.

According to an advantageous embodiment, the hydrogenated starch hydrolysates conforming to the invention have a concentration of products with a degree of polymerization (DP) equal to 7 of between 0.2 and 5%, preferably between 0.2 and 4%, and still more preferably between 0.2 and 3.5% by weight.

According to an even more advantageous embodiment, the hypocariogenicity of the hydrogenated starch hydrolysates conforming to the invention is even more marked if the latter have a concentration of products with a degree of polymerization (DP) greater than 20 which can be hydrolysed by amyloglucosidase under the conditions of the F test described above, of less than 5%, preferably less than 4%, still more preferably less than 3%.

The composition of the HSHs conforming to the invention, and in particular the concentrations of products corresponding to DP1, DP2, DP7 and DP20, may be determined in a completely conventional manner by high performance liquid chromatography.

To prepare the hydrogenated starch hydrolysates conforming to the invention, the procedure is carried out as follows or in a similar manner.

A starch prehydrolysate with a DE (dextrose equivalent) of between 6 and 20, preferably between 7 and 12, obtained by the acidic and/or enzymatic route, is mixed with at least one dextrin and/or polyglucose, and this mixture is subjected to an enzymatic treatment comprising at least the action of a β-amylase, the conditions for this treatment being chosen such that the DE of the hydrolysate obtained at the end of this treatment is between 35 and 75, preferably between 40 and 70, the hydrolysate obtained then being hydrogenated and then purified in a manner known per se.

The term "polyglucose" is understood to mean the products predominantly consisting of 1–6 bonds obtained by condensation or rearrangement, from glucose or from one or more optionally reduced sugars, under the combined action of heat and acids in a medium practically devoid of water. Such polymers have been described many times and may be obtained by processes such as those described in particular in U.S. Pat. Nos. 2,436,967; 3,766,165; 4,965,354; 5,051,500; JP 01-12761 and JP 02-163101. Advantageously, these polymers are obtained from glucose and citric acid, optionally in the presence of sorbitol.

The term "dextrin" is understood to mean the products obtained by heating starch adjusted to a low moisture level, generally in the presence of acidic or basic catalysts. This "dry roasting" of the starch, most commonly in the presence of an acid, brings about both a depolymerisation of the starch and a condensation of the starch fragments obtained, and results in the production of highly branched molecules. Dextrins are among the oldest starch derivatives and their preparation, their applications, the various types of dextrins as well as their properties are described for example in the book entitled "Starch Chemistry and Technology"—Second Edition—Edited by Roy L. WHISTLER—1984—Academic Press Inc.

Preferably, dextrins obtained by dry roasting of starch in the presence of an acidic catalyst such as hydrochloric acid are used for the preparation of the HSHs conforming to the invention. The acid is thus sprayed on the starch and the mixture obtained is predried, for example, from 80° to 130° C. until a water content of less than or equal to about 5% is obtained. The mixture is then "roasted" at a temperature of about 140° to 250° C. for a period of 30 minutes to about 6 hours in order to obtain the dextrin which has at the end of the reaction a DE of about 0.5 to 10. Any type of starch, and in particular maize starch, potato starch, wheat starch or cassava starch can be used for the preparation of these dextrins.

According to the ISO 1227 standard of 1979, a dextrin is obtained from starch or starch flour converted by heating in the dry state with or without the addition of small amounts of chemical reagents. Traditionally, dextrins are classified into two categories: white dextrins, whose appearance is not very different from that of the raw material used, and yellow dextrins, which are produced under more drastic conditions and whose depth of color can be correlated with the degree of modification of the native structure. The four types of reaction occurring during the dextrinization are, at low temperatures, essentially hydrolysis of the alpha 1–4 bonds, and then at higher temperatures, condensation, transglycosidation and anhydrization reactions.

Dextrins such as those marketed by the applicant company under the trade mark TACKIDEX DF 165, TACKIDEX DF 155, TACKIDEX JO 55 K may be advantageously used within the scope of the present invention.

The proportion of dextrin and/or polyglucose in the starch prehydrolysate-dextrin mixture subjected to the enzymatic hydrolysis is generally, in this process, between 5 and 95% by weight, these percentages being expressed in dry matter/dry matter. Preferably, this proportion is between 10 and 90%, and still more preferably between 15 and 75%.

In some cases, by selecting specific types of dextrins, in particular by selecting hardly processed dextrins, it is possible to obtain an HSH composition conforming to the invention by carrying out the enzymatic attack, comprising at least a β-amylase attack, directly on the pure dextrins.

On the other hand, a treatment with β-amylase alone may be sufficient in order to obtain an HSH corresponding to the composition defined in the present invention. But this β-amylase treatment may be preceded, accompanied or followed by a treatment using an α-amylase. According to a particularly advantageous embodiment of the invention, the hydrolysate obtained following the β-amylase, and optionally the α-amylase action is also subjected to the action of an enzyme which hydrolyses the 1–6 bonds of amylopectin, as is the case for isoamylase and pullulanase. This action of the enzyme hydrolysing the 1–6 bonds of amylopectin has the advantage of allowing only the polysaccharides which are very difficult to digest enzymatically, to remain in the hydrolysate obtained after its action. The action of the enzyme hydrolysing the 1–6 bonds may also precede or accompany the β-amylase treatment.

Processes consisting in enzymatically hydrolysing a dextrin have already been proposed in the literature.

Thus, European Patent Application no. 0,368,451 describes a process essentially consisting in dissolving a pyrodextrin in water and in allowing an α-amylase to act on the resulting solution. The aim of this process is to remove the undesirable odor and taste from the pyrodextrin and to give dextrins containing dietary fibers.

Thus, according to the process described in this patent application, a pyrodextrin is dissolved in water and then hydrolysed with α-amylase. Other enzymes can however be added after the α-amylase treatment: this is the case for transglucosidase, β-amylase, glucoamylase or amyloglucosidase. The product obtained at the end of this enzymatic treatment can then be hydrogenated. Monosaccharides and oligosaccharides may be added to the initial starch intended to be dextrinized, in order to increase the indigestible dextrin concentration of the final product.

The object of the abovementioned patent application is therefore essentially to provide a product which is not very digestible, "low in calories", which acts as dietary food fiber, and which essentially consists of polysaccharides which are not very digestible. The contents of the products exemplified by "indigestible dextrin" thus ranges between 27% and about 95%, and the concentration of polysaccharides with a degree of polymerization equal to or greater than 4 in these products is between about 60% and about 92% by weight.

Another process for producing dietary food fibers from dextrins is moreover described in Japanese Patent Application JP-A-62091501. This process consists in treating a hydrogenated starch hydrolysate at high temperature by carrying out this heating under anhydrous conditions at 150°–250° C., in the presence of a catalyst consisting of an inorganic acid or an organic acid.

Just like the patent application mentioned above, this document therefore relates to the production of products which are not very digestible in the body, so-called "low in calories", and which act in the body as food fibers. Their object is therefore very different from the object of the present invention, which is to prepare a sweetening product consisting of a hydrogenated starch hydrolysate with a high sweetening power, which is hypocariogenic and has technological features which can be used both in sweets, chewing gums and toothpastes, and in drinks and pharmaceutical or veterinary elixirs.

Moreover, it can be emphasized that the said documents do not describe or suggest the use of enzymes which hydrolyse the 1–6 bonds of amylopectin. By virtue of the anticipated action of these enzymes within the framework of the present invention, HSHs containing hydrogenated polysaccharides with a very low digestibility and a very low cariogenicity are obtained, which constitutes a great advantage.

Hydrogenation of the hydrolysate obtained following the enzymatic hydrolysis of the dextrin and/or polyglucose mixture and the starch prehydrolysate can be carried out in a manner known per se, by hydrogenation over Raney nickel or by hydrogenation over noble metals. This hydrogenation is carried out after purification of the hydrolysate, for example by treatment over activated carbon, after demineralization over cationic and anionic resins, and decolorization where appropriate. The hydrogenation may be carried out for example over a Raney nickel catalyst, at a temperature of 130° C. and at a hydrogen pressure of 50 bars.

After hydrogenation, the syrup of hydrogenated starch hydrolysate obtained is filtered, then demineralized and then concentrated until the commercial concentration is obtained, which is generally between about 70 and 85 Brix, equivalent to a dry matter of between 70 % and 85%. The hydrogenation is carried out until a percentage of residual reducing sugars over dry matter of less than 0.50, preferably less than 0.25 and still more preferably less than 0.20 is obtained.

The viscosity of the hydrogenated starch hydrolysates conforming to the invention is generally 1000 to 20,000 centipoises at 20° C. and at 74% dry matter.

One of the essential qualities of the hydrolysates according to the invention lies in their hypocariogenicity, that is to say in their capacity to cause a much lower acidification by the bacteria present in the mouth than ordinary conventional sugars such as glucose, fructose, sucrose or glucose syrups.

According to a completely advantageous embodiment of the invention, the hydrogenated starch hydrolysates have the property of being able to be qualified as non-cariogenic according to a B test.

This B test was developed by the applicant company in order to monitor the non-cariogenic character of the hydrogenated hydrolysates marketed from 1978 under the name LYCASIN 80/55. This simple test is based on the determination in vitro of the acidification of a given amount of hydrogenated starch hydrolysate after inoculating the medium with saliva. It is based on the determination of the drop in pH over time for a culture broth containing the test product, after then inoculating with saliva obtained from several donors, compared with a control culture broth not containing any carbohydrate. It should be emphasized that this test is not sufficient to characterize in an absolute manner the non-cariogenicity of a product because its results can vary for example with the quality of the saliva used, but it makes it possible, nevertheless, to establish valid comparisons between the different products.

The detailed procedure for this test is as follows.

A series of tubes are prepared containing 10 ml of a sugar-free nutrient culture medium (trypticae medium containing 2% dry matter) at pH 7, and these tubes are sterilized by transferring to an autoclave at 120° C. for 20 minutes.

In a first series of five tubes, 1 ml of sterile water is introduced to make a control series.

In a second series of five tubes, 1 ml of a solution containing 18% (w/v) of the test product is introduced.

Then, the five tubes in each series are inoculated with the same volume of 0.2 ml per tube of a five-fold dilution of human saliva obtained by collecting from five donors.

The formation of acids is then monitored by measuring the pH, a first measurement being carried out before incubation and the other measurements being carried out after incubations at 30° C. of 3, 6, 13, 18 and 21 hours respectively.

For a product to be considered as non-cariogenic based on this B test, the difference in pH observed between the control after 21 hours and the test product after 21 hours should not be too pronounced and, in practice, not more than one unit of pH.

One of the great merits of the present invention is that it provides hydrogenated starch hydrolysates which exhibit the property of being non-cariogenic based on this B test, even though they contain nevertheless a substantial amount of oligosaccharides and polysaccharides.

Preferably, the amounts and conditions for the action of the various enzymes mentioned above and which may be used for preparing the starch hydrolysate intended for subsequent hydrogenation, are chosen from the following:

β-amylase: 100 to 10,000 LINTNER units per kilogram of dry substrate, temperature of 50° C. to 60° C., duration of action from 30 to 100 hours, pH of 5.0 to 6.0, α-amylase: 20 to 2000 KNU units (kilo NOVO units) per kilogram of dry substrate, pH of 5.0 to 6.0, temperature of 50° C. to 60° C., duration of action from 16 to 100 hours, enzyme hydrolysing the 1–6 bonds: 150 to 15,000 ABM units (ABM, Cheshire, England) per kilogram of dry substrate, optionally in the presence of 10 to 500 LINTNER units of β-amylase per kilogram of dry substrate, pH 5.0 to 6.0, temperature of 50° C. to 60° C., duration of action from 24 to 100 hours.

The enzymes which may be used may be:

in the case of β-amylase, β-amylase of microbial or plant origin, in the case of α-amylase, bacterial or fungal α-amylases, in the case of those hydrolysing the 1–6 bonds, those chosen from pullulanase and isoamylase, such as for example PULLUZYME from ABM or CK 20 L from AMANO.

As raw material for the preparation of the prehydrolysate which is mixed with dextrin and/or polyglucose, all types of starch may be used including in particular maize starch, potato starch, cassava starch, wheat starch, rice starch and pea starch.

Of course, in order to prepare the hydrogenated starch hydrolysates conforming to the invention, it is possible, instead of carrying out the enzymatic hydrolysis on the mixture Of starch prehydrolysate and dextrin and/or polyglucose, to perform the optionally different enzymatic actions on each of these components separately, and then to mix subsequently the products obtained in the desired proportions in order to obtain a starch hydrolysate which, after hydrogenation, corresponds to the appropriate composition.

Likewise, it is evident that the composition in question can be obtained by mixing components which are already hydrogenated.

DESCRIPTION OF THE PREFERRED EMBODIMENTS

The invention will be understood more clearly with the aid of the following examples.

EXAMPLE 1

Into 25 liter tanks, stirred and thermostatted, are introduced 12 liters of a syrup consisting, on a dry basis, of:

Example 1a

80% of maize starch liquefied to a DE of 11.2 by double liquefaction using the thermoresistant alpha-amylase TERMAMYL from NOVO and 20% of the yellow dextrin TACKIDEX DF 165 marketed by the applicant company.

Example 1b

55% of the maltodextrin GLUCIDEX 6 B, also marketed by the applicant company, obtained by enzymatic hydrolysis of a maize starch until a DE equal to 6 is obtained, and 45% of the same yellow dextrin TACKIDEX DF 165.

Example 1c

100% of the yellow dextrin TACKIDEX DF 165.

Comparative Example 1d

100% of maize starch liquefied to a DE of 8.0.

Comparative Example 1e

100% of maize starch liquefied to a DE of 6.0. All these syrups were adjusted to a dry matter in the region of 35% by a simple Brix-meter reading.

The pH values were adjusted to 5.5 using hydrochloric acid or sodium hydroxide, the tanks were thermostatted at 55° C., and then the following were added thereto:

Example 1a 0.018% by weight per dry weight of β-amylase of the trade mark SPEZYME DBA marketed by GENENCOR, 0.2% by weight per dry weight of pullulanase of the trade mark PULLUZYME 750 L marketed by A.B.M. as well as 0.02% of the α-amylase MAXAMYL HT 3000 from GIST. After 24 hours of saccharification, 0.1% by weight per dry weight of α-amylase of the trade mark MAXAMYL was added.

After 72 hours, the saccharification was stopped by acidification to pH 3.5 and heating to 80° C. and the syrups obtained were purified in a conventional manner by treatment with activated carbon and demineralization over cationic and anionic resins.

Example 1b 0.015% of β-amylase of the trade mark SPEZYME DBA, 0.2% of the pullulanase PULLUZYME 750 L.

After 40 hours of saccharification, 0.1% of α-amylase was added and this addition was repeated after 68 hours of saccharification.

The saccharification was stopped after 88 hours and the syrup was purified.

Example 1c 0.015% of the β-amylase SPEZYME DBA.
0.2% of the pullulanase PULLUZYME 750 L.

After 48 hours of saccharification, 0.1% of the α-amylase MAXAMYL HT 3000 was added.

The saccharification was stopped after 88 hours and then the syrup was purified.

Comparative Example 1d 0.02% by weight/weight of the β-amylase SPEZYME DBA, and then after 24 hours of saccharification, 0.1% by weight/weight of the α-amylase MAXAMYL HT 3000 was added thereto.

The saccharification was stopped after 72 hours and then syrup was purified.

Comparative Example 1e 0.05% by weight of the β-amylase SPEZYME DBA and 0.2% of the pullulanase PULLUZYME 750 L.

The saccharification was stopped after 48 hours and then the syrup was purified.

The purified syrups obtained according to examples 1b and 1c were then treated by adding hydrogen peroxide (0.8% by volume/volume of a solution of $H_2O_2$ at 35% (v/v), for 24 hours, at 70° C. and pH 9.5). The residual hydrogen peroxide was decomposed by adding a small amount of catalase and then the syrups were deoxygenated under vacuum before being again treated with a small amount of activated carbon and then demineralized over a bed of mixed resins.

All the syrups were then concentrated to a dry matter of about 40% and were then hydrogenated using 5% of Raney nickel catalyst, at a temperature of 130° C. at a hydrogen pressure of 50 bars. The hydrogenation was continued until a reducing sugar level of less than 0.5% was obtained.

The syrup 1c, assaying 15.3% of maltitol, 22.4% of polysaccharides with a DP >20, 16.2% of non-hydrolyzable polysaccharides according to the F test, 38.2% of precipitate P1 in ethanol and 7.7% of precipitate P2 after enzymatic digestion according to the A test, was then supplemented with crystallized maltitol in a proportion such that this added maltitol represents 40% of the dry matter of the syrup, in order to constitute the HSH 1c according to the invention.

The HSHs obtained according to example 1a and example 1b, and the HSH 1c were then filtered, demineralized and then concentrated to a dry matter of about 75%.

Figure 1:
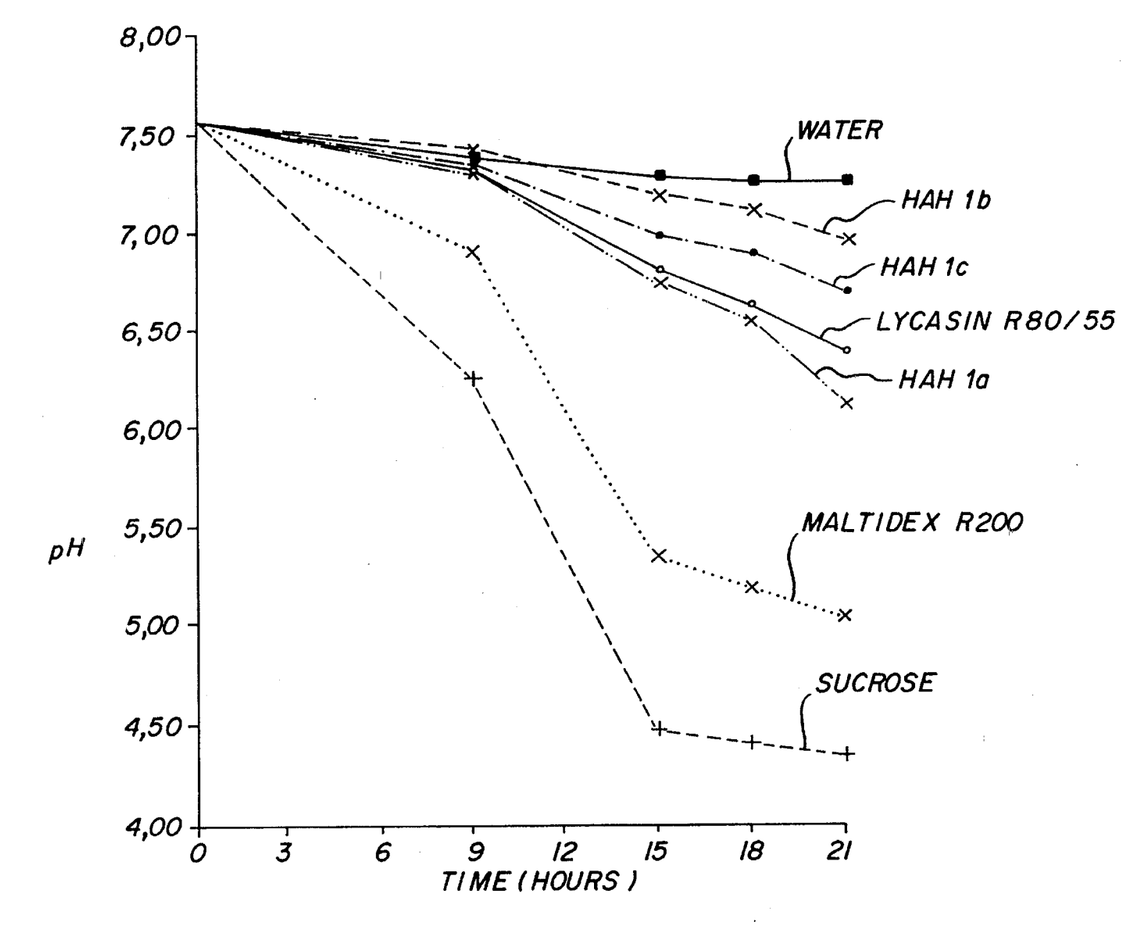
FIG. 1 shows a comparison of the acidogenic power in vitro of various compounds.

These HSHs showed the following carbohydrate spectra after which the results obtained in the F test and in the A test (TABLE I) and a pH profile according to the caries pretest B (FIG. 1) are represented.

TABLE I

| | PRODUCTS ACCORDING TO THE INVENTION | | | COMPARATIVE EXAMPLES | |
|---|---|---|---|---|---|
| | HSH 1a | HSH 1b | HSH 1c | HSH 1d | HSH 1e |
| Dry matter | 75 | 76 | 76 | 75 | 75 |
| Reducing sugars (% over DM) | 0.14 | 0.03 | 0.24 | <0.1 | <0.1 |
| DP1 (sorbitol) | 3.4 | 3.1 | 2.5 | 3.7 | 3 |

TABLE I-continued

|  | PRODUCTS ACCORDING TO THE INVENTION | | | COMPARATIVE EXAMPLES | |
|---|---|---|---|---|---|
|  | HSH 1a | HSH 1b | HSH 1c | HSH 1d | HSH 1e |
| DP2 (maltitol and isomaltitol) | 49.6 | 46.3 | 48.9 | 54.5 | 78.4 |
| DP3 | 21.7 | 17.3 | 4.4 | 20 | 10 |
| DP4 | 2.0 | 3.7 | 2.5 | 1.0 | 3 |
| DP5 | 3.1 | 3.0 | 3.0 | 3.8 | 1.7 |
| DP6 | 2.4 | 2.2 | 2.5 | 3.9 | 0.4 |
| DP7 | 1.5 | 2.0 | 2.7 | 2.6 | 0.6 |
| DP8 | 0.9 | 1.9 | 2.6 | 1.7 | 0.3 |
| DP9–20 | 7.8 | 11.5 | 15.5 | 7.5 | 1.7 |
| DP > 20 | 7.3 | 8.7 | 13.8 | 1.0 | 0.9 |
| Polysaccharides not hydrolysed by amyloglucosidase (in %) (F test) | 3.1 | 5.0 | 8.7 | 0.1 | 0.0 |
| Precipitate P1 in ethanol (in %) | 10.4 | 12.7 | 23.0 | 0.0 | 0.0 |
| Precipitate P2 (%) after enzymatic digestion (A test) | 3.4 | 2.9 | 4.6 | 0.0 | 0.0 |
| Viscosity 20° C. (cps) | 4100 | 4800 | 7000 | 2000 | 1800 |

EXAMPLE 2

PREPARATION OF HYDROGENATED STARCH HYDROLYSATE CONFORMING TO THE INVENTION WITH ENZYMATIC HYDROLYSIS WITHOUT THE ACTION OF AN ENZYME HYDROLYSING THE 1–6 BONDS OF AMYLOPECTIN

Into a 25-liter tank, stirred and thermostatted, are introduced 12 liters of a syrup consisting, relative to the dry matter, of 80% of maize starch liquefied to a DE of 12.9 by double liquefaction using the thermoresistant α-amylase TERMAMYL 120 L from NOVO and 20% of TACKIDEX JO 55K, a dextrin obtained by acidic conversion of maize starch, marketed by the applicant company. This dextrin is thought to contain 3.4% of reducing sugars relative to the dry matter.

The saccharification was carried out by adding to the said mixture obtained, 0.02% by weight/weight of the α-amylase MAXAMYL HT 3000 and 0.018% weight/weight of the β-amylase SPEZYME DBA. After 24 hours of saccharification at a temperature of 55° C. and a pH of 5.5, 0.1% weight/weight of a α-amylase MAXAMYL HT 3000 is added. The saccharification is stopped after 70 hours and the syrup is purified. The syrup thus obtained is then hydrogenated under the same conditions as those described in example 1. The hydrogenated starch hydrolysate obtained has the composition given in Table II.

TABLE II

| Hydrogenated starch hydrolysate HSH 1f | |
|---|---|
| Dry matter | 75% |
| Reducing sugars | 0.15% |
| DP1 (Sorbitol) | 2.2% |
| DP2 (Maltitol and Isomaltitol) | 51.0% |
| DP3 | 17.2% |
| DP4 | 0.9% |
| DP5 | 2.9% |

TABLE II-continued

| Hydrogenated starch hydrolysate HSH 1f | |
|---|---|
| DP6 | 3.9% |
| DP7 | 3.2% |
| DP8 | 2.6% |
| DP9 | 1.1% |
| DP10–20 | 10.4% |
| DP > 20 | 4.7% |
| Non-hydrolyzable polysaccharides according to the F test (in %) | 1.2% |
| Precipitate P1 in ethanol (in %) | 12.2% |
| Precipitate P2 (in %) after enzymatic digestion (A test) | 2.9% |
| Viscosity at 20° C. (in cps) | 4300 |

EXAMPLE 3

PREPARATION OF A HYDROGENATED STARCH HYDROLYSATE UNDER THE SAME CONDITIONS AS THE HSH 1a BUT WITHOUT THE ACTION OF PULLULANASE

The same preparation conditions as those adopted for the preparation of the hydrogenated starch hydrolysate HSH 1a described in example 1 are used except for the fact that during the saccharification, the addition of a 0.2% by weight/dryweight of pullulanase of the trade mark PULLUZYME is omitted.

The other conditions are otherwise equal. The composition of the HSH 1g thus obtained is presented in Table III below.

TABLE III

| Dry matter | 75% |
|---|---|
| Reducing sugars | 0.10% |
| DP1 (Sorbitol) | 2.3% |
| DP2 (Maltitol and Isomaltitol) | 49.8% |
| DP3 | 15.4% |
| DP4 | 1.0% |
| DP5 | 3.2% |
| DP6 | 3.7% |
| DP7 | 3.1% |
| DP8 | 2.5% |
| DP9 | 1.1% |
| DP10–20 | 11.2% |
| DP > 20 | 6.8% |
| Non-hydrolyzable polysaccharides according to the F test (in %) | 2.8% |
| Precipitate P1 in ethanol (in %) | 13.5% |
| Precipitate P2 (in %) after enzymatic digestion (A test) | 3.1% |
| Viscosity at 20° C. (in cps) | 4900 |

It can be seen by comparing the compositions of the hydrogenated starch hydrolysates HSH 1a and HSH 1g (the latter thus being obtained without the action of pullulanase), that the percentage of DP of between 10 and 20 increases from 7.0 to a value of 11.2%, the value for DPs greater than 20 being approximately identical. The percentage of polysaccharides which can be precipitated in ethanol increases from 10.4 to 13.5%.

EXAMPLE 4

Into a 25-liter tank, stirred and thermostatted, are suspended, in 20 liters of boiling water, about 2.3 kg of maltose of the trade mark Sunmalt (marketed by the company HAYASHIBARA) and 3.7 kg of polydextrose A (marketed by the company PFIZER). The pH is adjusted to 5.5 by the addition of sodium hydroxide.

The mixture is adjusted to a temperature of 55° C. 0.06% (w/dry weight) of the fungal α-amylase MKC LF 40 from Miles is then added, and then the saccharification is allowed to proceed for 48 hours.

The syrup obtained is heated at 80° C. for 20 minutes in order to inhibit the enzymes, and then purified using activated carbon before being demineralized over strong cationic and weak anionic resins.

The syrup is then concentrated to a dry matter of 40% and then hydrogenated as described in example 1 before being purified and concentrated.

The final syrup has:

a sorbitol concentration of 6.9% a maltitol concentration of 36.7% a non-hydrolyzable polysaccharide concentration according to the F test of 2.5%

The concentration of reducing sugars is particularly low since it is less than 0.1%.

molds after cooling to around 130° C. They are then cooled to room temperature and then removed from the molds.

The various boiled sweets obtained were compared both from the point of view of their color and their stability to moisture and heat.

With boiling at 140° C., it is not possible to obtain with these syrups a glassy and non-sticky structure for the sweets. The sweets prepared with the HSH 1c began to become colored at boiling temperatures as high as or exceeding 190° C., but it is not necessary to reach this temperature in order to manufacture satisfactory sweets with this hydrolysate.

Table IV collates the data relating to the regain of water by the sweets obtained, this water regain being achieved by keeping the sweets at 66% relative humidity and at 20° C. and measured by weighing the sweets. The hygroscopicity is expressed over a period of 5 days according to the formula:

$$H5 = \frac{\text{water regain after 13 days} - \text{water regain after 8 days}}{5}$$

It can be observed that the products obtained from the HSHs 1a, 1b and in particular 1c make it possible to obtain boiled sweets which are less hygroscopic than those produced with HSH 1d. The best results are obtained with HSH 1c, with boiling at 160° C.

TABLE IV

| BOILING TEMPERATURE | PRODUCTS ACCORDING TO THE INVENTION | | | | | | | |
|---|---|---|---|---|---|---|---|---|
| | HSH 1a | | HSH 1b | | HSH 1c | | HSH 1d | |
| | H5 | H11 | H5 | H11 | H5 | H11 | H5 | H11 |
| 160° | 0.38 | 0.45 | 0.32 | 0.33 | 0.25 | 0.26 | 0.41 | 0.43 |
| 180° | 0.34 | 0.36 | 0.34 | 0.35 | 0.25 | 0.26 | 0.40 | 0.42 |
| 200° | 0.32 | 0.34 | 0.35 | 0.36 | 0.26 | 0.27 | 0.42 | 0.44 |

EXAMPLE 5

COMPARATIVE EXAMPLE RELATING TO THE USE OF THE SYRUPS ACCORDING TO THE INVENTION IN MANUFACTURE OF SUGAR-FREE BOILED SWEETS

Sugar-free boiled type sweets were prepared from the following four syrups:

HSH 1a

HSH 1b

HSH 1c

HSH 1d whose composition was given in example 1.

These four HSHs were dehydrated by boiling at atmospheric pressure at the following four temperatures: 140° C., 160° C., 180° C. and 200° C., and then poured into teflon The various boiled sweets obtained were also compared with respect to their thermal properties indicating their plastic flow (cold flow) tendency.

The water contents and the glass transition temperatures of the various sweets obtained within the scope of this example are therefore presented in Table V.

Comparison between the products according to the invention and HSH 1d shows that, for fairly similar maltitol concentrations, close to 50%, the products according to the invention make it possible to prepare the best sweets. Indeed, high glass transition temperatures with low boiling temperatures are obtained. For example, to achieve a glass transition temperature of 45° C., it is enough to boil the HSH 1c at 160° C. whereas HSH 1d has to be boiled at 200° C., which represents a very sharp reduction in the cost of production of these boiled sweets.

Moreover, the products obtained are less hygroscopic since for the same glass transition temperature, they contain more water.

TABLE V

| BOILING TEMPERATURE (°C.) | PRODUCTS ACCORDING TO THE INVENTION | | | | | | | |
|---|---|---|---|---|---|---|---|---|
| | HSH 1a | | HSH 1b | | HSH 1c | | HSH 1d | |
| | Water content* | Tg* | Water content | Tg | Water content | Tg | Water content | Tg |
| 140° C. | — | — | 4.20 | 25.3 | 4.20 | 26.6 | — | — |
| 145° C. | — | — | 3.60 | 29.2 | 3.30 | 35.0 | — | — |
| 150° C. | — | — | 3.00 | 34.8 | 2.55 | 42.3 | 2.50 | 24.0 |

TABLE V-continued

| | PRODUCTS ACCORDING TO THE INVENTION | | | | | | |
|---|---|---|---|---|---|---|---|
| BOILING | HSH 1a | | HSH 1b | | HSH 1c | | HSH 1d | |
| TEMPERATURE (°C.) | Water content* | Tg* | Water content | Tg | Water content | Tg | Water content | Tg |
| 160° C. | 2.60 | 36.8 | 2.15 | 41.5 | 1.95 | 46.4 | 2.35 | 29.0 |
| 180° C. | 1.60 | 46.2 | 1.35 | 50.0 | 1.45 | 53.1 | 1.35 | 39.0 |
| 200° C. | 0.80 | 53.6 | 0.90 | 55.8 | 0.95 | 59.4 | 0.70 | 44.0 |

*Water content: final water content of the sweet in % (w/w)
*Tg = glass transition temperature in °C.

EXAMPLE 6

PREPARATION OF COUGH SYRUPS

Cough syrups were prepared using the following five sweet excipients:

a sucrose syrup containing 64% of dry matter the HSH 1b according to the invention the HSH 1c according to the invention the HSH 1d the product MALTIDEX® 200, marketed by the company CERESTAR, which is a hydrogenated starch hydrolysate containing 75% dry matter, whose carbohydrate spectrum is given in Table VI:

TABLE VI

| SORBITOL | 2.2% |
|---|---|
| MALTITOL | 53.7% |
| DP3 | 16.8% |
| DP4 | 1.1% |
| DP5 | 0.7% |
| DP6 | 0.9% |
| DP7 | 1.2% |
| DP8 | 2.4% |
| DP9 | 2.8% |
| DP 10–20 | 8.3% |
| DP > 20 | 9.5% |
| Non-hydrolyzable polysaccharides according to the F test (in %) | 0.2% |
| Precipitate P1 in ethanol (in %) | 13% |
| Precipitate P2 (in %) after enzymatic digestion according to the A test | 0.7% |

The syrups were prepared according to the following formulae (see Table VII) by adding into a container heated to 40° C. and stirred, glycerin and water, and then guaifenesin, dextromethorphan hydrobromide, sodium benzoate, optionally saccharin, the sweet excipient, citric acid, sodium citrate, coloring, menthol dissolved in alcohol, and then flavoring. Water was then added in sufficient amount and then the syrups were filtered and bottled.

TABLE VII

| | SYRUP 1 | SYRUP 2 | SYRUP 3 | SYRUP 4 | SYRUP 5 |
|---|---|---|---|---|---|
| DEXTROMETHORPHAN, HB2 | 0.1 | 0.1 | 0.1 | 0.1 | 0.1 |
| GUAIFENESIN | 2.0 | 2.0 | 2.0 | 2.0 | 2.0 |
| ALCOHOL | 5.3 | 5.3 | 5.3 | 5.3 | 5.3 |
| ANHYDROUS CITRIC ACID | 0.14 | 0.14 | 0.14 | 0.14 | 0.14 |
| GLYCERIN | 10 | 10 | 10 | 10 | 10 |
| SODIUM BENZOATE | 0.1 | 0.1 | 0.1 | 0.1 | 0.1 |
| SACCHARIN | | 0.2 | 0.2 | 0.2 | 0.2 |
| FD AND C RED 40 COLORING | 0.003 | 0.003 | 0.003 | 0.003 | 0.003 |
| MENTHOL | 0.01 | 0.01 | 0.01 | 0.01 | 0.01 |
| CHERRY FLAVOR | 0.3 | 0.3 | 0.3 | 0.3 | 0.3 |
| SODIUM CITRATE | 0.38 | 0.38 | 0.38 | 0.38 | 0.38 |
| SUCROSE SYRUP | 87.9 | | | | |
| HSH 1b | | 75 | | | |
| HSH 1c | | | 75 | | |
| HSH 1d | | | | 75 | |
| MALTIDEX 200 | | | | | 75 |
| WATER | QSP | | 100 ml | | |

A test panel consisting of 10 persons noted the characteristics of these four syrups in terms of taste and texture.

In terms of taste, all the syrups were assessed in the same manner, the perception of the intensity of sweetness being comparable and sufficient to disguise the bitterness of the active ingredients in all cases.

In terms of texture, the smoothness in the mouth is much more marked for the syrups obtained with the HSHs 1b and 1c according to the invention. The syrups obtained with the products HSH 1b, HSH 1c and HSH 1d are not cariogenic based on the B test, whereas the syrups prepared using sucrose and MALTIDEX® 200 are.

EXAMPLE 7

PREPARATION OF CHEWING GUMS

Chewing gums without cariogenic sugars and without intense sweeteners were prepared using the HSH 1c composition according to the invention.

For that, the following are introduced sequentially and at 2 minute intervals into a kneading machine comprising two Z-shaped arms previously heated to 45° C. and switched on:

- 270 g of base gum of the 34/42 type (marketed by the company DREYFUS) previously softened at 55° C.,
- 200 g of sorbitol powder of the trade mark NEOSORB® P60W marketed by the applicant company, and 20 g of glycerin,
- 100 g of mannitol F marketed by the applicant company and 50 g of HSH 1c, premixed,
- 218 g of sorbitol powder of the trade mark NEOSORB P60W and 50 g of HSH 1c, premixed, and finally, after mixing for 5 minutes,
- 27.5 g of ground xylitol of the trade mark XYLISORB®, marketed by the applicant company, 25 g of vitamin C, 2.5% of citric acid, 1.0 g of an orange-colored aqueous solution of colorings and 8.0 g of mandarin flavour.

After kneading for three minutes, the chewing gum paste was flattened and shaped using mannitol F as dusting powder.

Chewing gums of soft texture were thus obtained possessing the correct flavour and having, surprisingly, a more intense sweet taste than that of the polyol-containing chewing gums on the market not containing an intense sweetener.

I claim:

1. A hypocariogenic hydrogenated hydrolyzate produced by an enzymatic hydrolysis with at least the action of beta-amylase of a mixture containing at least a dextrin or polyglucose, said polyglucose predominantly consisting of 1–6 bonds, obtained by condensation or rearrangement of glucose or one or more other sugars, followed by hydrogenation of the resulting hydrolyzate, said hydrogenated hydrolyzate comprising, the concentrations being expressed by weight relative to the dry matter of the hydrolyzate, 0.1 to 19% of sorbitol,
   35 to 87% of maltitol,
   1 to 17% by weight of polysaccharides which are not hydrolyzed by amyloglucosidase in an F test,
   the balance for 100% consisting of hydrogenated oligo- or polysaccharides.

2. The hydrolyzate according to claim 1, wherein the concentration by weight of said polysaccharides which are not hydrolyzed by amyloglucosidase in an F test is of 1.5 to 15%.

3. The hydrolyzate according to claim 1, wherein the concentration by weight of said polysaccharides which are not hydrolyzed by amyloglucosidase in an F test is of 2 to 12%.

4. The hydrolyzate according to claim 1, wherein the sorbitol concentration is between 1 and 17% by weight.

5. The hydrolyzate according to claim 1, wherein the sorbitol concentration is between 2 and 16% by weight.

6. The hydrolyzate according to claim 1, wherein the maltitol concentration is between 40 and 82% by weight.

7. The hydrolyzate according to claim 1, wherein the maltitol concentration is between 45 and 77% by weight.

8. The hydrolyzate according to claim 1, wherein the concentration of polysaccharides with a degree of polymerization equal to 7 is between 0.2 and 5% by weight.

9. The hydrolyzate according to claim 1, wherein the concentration of polysaccharides with a degree of polymerization equal to 7 is between 0.2 and 4% by weight.

10. The hydrolyzate according to claim 1, wherein the concentration of polysaccharides with a degree of polymerization equal to 7 is between 0.2 and 3.5% by weight.

11. The hydrolyzate according to claim 1, wherein the hydrolyzate has a concentration of polysaccharides with a degree of polymerization greater than 20, which can be hydrolysed by amyloglucosidase under the conditions of the F test, of less than 5%.

12. The hydrolyzate according to claim 1, wherein the hydrolyzate has a concentration of polysaccharides with a degree of polymerization greater than 20, which can be hydrolysed by amyloglucosidase under the conditions of the F test, of less than 4%.

13. The hydrolyzate according to claim 1, wherein the hydrolyzate has a concentration of polysaccharides with a degree of polymerization greater than 20, which can be hydrolysed by amyloglucosidase under the conditions of the F test, of less than 3%.

14. A hypocariogenic hydrogenated hydrolyzate produced by an enzymatic hydrolysis with at least the action of beta-amylase of a mixture containing at least a dextrin or a polyglucose predominantly consisting of 1–6 bonds, obtained by condensation or rearrangement of glucose or one or more other sugars, followed by hydrogenation of the resulting hydrolyzate, said hydrogenated hydrolyzate comprising, the concentrations being expressed by weight relative to the dry matter of the hydrolyzate, 0.1 to 19% of sorbitol,
   35 to 87% of maltitol,
   1 to 17% by weight of polysaccharides which can be precipitated in ethanol and are not hydrolyzed by amyloglucosidase in an A test,
   the balance for 100% consisting of hydrogenated oligo- or polysaccharides.

15. The hydrolyzate according to claim 14, wherein the concentration by weight of said polysaccharides which are not hydrolyzed by amyloglucosidase in an A test is of 1 to 10%.

16. The hydrolyzate according to claim 14, wherein the concentration by weight of said polysaccharides which are not hydrolyzed by amyloglucosidase in an A test is of 1.5 to 8%.

17. The hydrolyzate according to claim 14, wherein the concentration by weight of said polysaccharides which are not hydrolyzed by amyloglucosidase in an A test is of 2 to 5%.

18. The hydrolyzate according to claim 14, wherein the sorbitol concentration is between 1 and 17% by weight.

19. The hydrolyzate according to claim 14, wherein the sorbitol concentration is between 2 and 16% by weight.

20. The hydrolyzate according to claim 14, wherein the maltitol concentration is between 40 and 82% by weight.

21. The hydrolyzate according to claim 14, wherein the maltitol concentration is between 45 and 77% by weight.

22. The hydrolyzate according to claim 14, wherein the concentration of polysaccharides with a degree of polymerization equal to 7 is between 0.2 and 5% by weight.

23. The hydrolyzate according to claim 14, wherein the concentration of polysaccharides with a degree of polymerization equal to 7 is between 0.2 and 4% by weight.

24. The hydrolyzate according to claim 14, wherein the concentration of polysaccharides with a degree of polymerization equal to 7 is between 0.2 and 3.5% by weight.

25. The hydrolyzate according to claim 14, wherein the hydrolyzate has a concentration of polysaccharides with a degree of polymerization greater than 20, which can be hydrolysed by amyloglucosidase under the conditions of the F test, of less than 5%.

26. The hydrolyzate according to claim 14, wherein the hydrolyzate has a concentration of polysaccharides with a degree of polymerization greater than 20, which can be hydrolysed by amyloglucosidase under the conditions of the F test, of less than 4%.

27. The hydrolyzate according to claim 14, wherein the hydrolyzate has a concentration of polysaccharides with a degree of polymerization greater than 20, which can be hydrolysed by amyloglucosidase under the conditions of the F test, of less than 3%.

* * * * *

UNITED STATES PATENT AND TRADEMARK OFFICE
CERTIFICATE OF CORRECTION

PATENT NO. : 5,493,014
DATED : February 20, 1996
INVENTOR(S) : CABOCHE

It is certified that error appears in the above-indentified patent and that said Letters Patent is hereby corrected as shown below:

Column 1, line 1, change "as" to --is--.

Column 1, line 24, change "heath" to --health--.

Column 1, line 28, change "hypocarogenic" to --hypocariogenic--.

Column 1, line 41, before "75/75" insert --MALTISORB--.

Column 2, line 11, change "-than" to --than--.

Column 6, line 40, delete "according to the invention".

Column 10, line 55, change "Of" to --of--.

Column 16, line 19, please insert --and over a period of 11 days according to fomula:

$$H_{11}= \frac{\text{water regain after 13 days - water regain after 2 days}}{11}$$ --

Signed and Sealed this

Sixteenth Day of July, 1996

Attest:

BRUCE LEHMAN

Attesting Officer

Commissioner of Patents and Trademarks